United States Patent
Kim et al.

(10) Patent No.: US 10,244,961 B2
(45) Date of Patent: Apr. 2, 2019

(54) WEARABLE DEVICE FOR MEASURING EDEMA INDEX AND METHOD OF MEASURING EDEMA INDEX USING SAME

(71) Applicant: Industry-Academic Cooperation Foundation, Chosun University, Gwangju (KR)

(72) Inventors: Youn Tae Kim, Daejeon (KR); Jae Hyo Jung, Gwangju (KR); Si Ho Shin, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 167 days.

(21) Appl. No.: 15/364,326

(22) Filed: Nov. 30, 2016

(65) Prior Publication Data
US 2018/0049666 A1 Feb. 22, 2018

(30) Foreign Application Priority Data
Aug. 22, 2016 (KR) ........................ 10-2016-0106397

(51) Int. Cl.
*A61B 5/00* (2006.01)
*A61B 5/053* (2006.01)

(52) U.S. Cl.
CPC .......... *A61B 5/0531* (2013.01); *A61B 5/4878* (2013.01); *A61B 5/681* (2013.01); *A61B 5/7275* (2013.01); *A61B 2562/0214* (2013.01)

(58) Field of Classification Search
CPC ... A61B 5/0531; A61B 5/7275; A61B 5/4878; A61B 5/681; A61B 2562/0214
See application file for complete search history.

(56) References Cited

U.S. PATENT DOCUMENTS

| | | | |
|---|---|---|---|
| 8,965,497 B2* | 2/2015 | Tournefier | A61B 5/0002 600/382 |
| 9,907,473 B2* | 3/2018 | Tran | H04B 1/3827 |
| 2009/0182204 A1* | 7/2009 | Semler | A61B 5/04085 600/301 |
| 2010/0168530 A1 | 7/2010 | Chetham et al. | |
| 2011/0224521 A1* | 9/2011 | Gericke | A61B 5/053 600/347 |

(Continued)

FOREIGN PATENT DOCUMENTS

| | | |
|---|---|---|
| JP | 2010-510835 A | 4/2010 |
| JP | 2010-526604 A | 8/2010 |

(Continued)

*Primary Examiner* — Sean P Dougherty
(74) *Attorney, Agent, or Firm* — Renner, Otto, Boisselle & Sklar LLP

(57) ABSTRACT

A wearable device for measuring an edema index includes: a band, wearable on a wrist; an electrode module including a pair of current electrodes and a pair of voltage electrodes; and a main module applying an alternating current (AC) to the pair of current electrodes, and obtaining an edema index of a human body from an AC voltage measured from the pair of voltage electrodes, wherein each of the pair of current electrodes and the pair of voltage electrodes is attached to one surface of the band in a row in a length direction of the band, and protrudes from the surface of the band to be in direct contact with the skin of the wrist when the band is worn on the wrist.

6 Claims, 5 Drawing Sheets

(56) References Cited

U.S. PATENT DOCUMENTS

| | | | |
|---|---|---|---|
| 2011/0245712 A1* | 10/2011 | Patterson | A61B 5/0535 600/547 |
| 2011/0251513 A1 | 10/2011 | Chetham et al. | |
| 2011/0282180 A1* | 11/2011 | Goldkuhl | A61B 5/0531 600/393 |
| 2012/0123232 A1* | 5/2012 | Najarian | A61B 5/0022 600/345 |
| 2012/0323134 A1* | 12/2012 | Cory | A61B 5/0536 600/547 |
| 2013/0165760 A1* | 6/2013 | Erlinger | A61B 5/04 600/382 |
| 2013/0172691 A1* | 7/2013 | Tran | A61B 8/488 600/301 |
| 2013/0303935 A1* | 11/2013 | Uchiyama | A61B 5/7278 600/547 |
| 2014/0276166 A1* | 9/2014 | Drori | A61B 5/0537 600/529 |
| 2015/0025353 A1* | 1/2015 | Salonius | A61B 5/0537 600/388 |
| 2015/0148641 A1* | 5/2015 | Morun | A61B 5/0492 600/372 |
| 2016/0128604 A1* | 5/2016 | Eom | A61B 5/0537 600/384 |
| 2016/0296136 A1* | 10/2016 | Jung | A61B 5/681 |
| 2018/0177430 A1* | 6/2018 | De Limon | A61B 5/0537 |

FOREIGN PATENT DOCUMENTS

| | | |
|---|---|---|
| KR | 1020060104792 A | 10/2006 |
| KR | 2007-0083334 A | 8/2007 |

* cited by examiner

WEARABLE DEVICE FOR MEASURING EDEMA INDEX AND METHOD OF MEASURING EDEMA INDEX USING SAME

CROSS-REFERENCE TO RELATED APPLICATION

This application claims the benefit of priority to Korean Patent Application No. 10-2016-0106397, filed on Aug. 22, 2016 with the Korean Intellectual Property Office, the entirety of which is incorporated herein by reference.

BACKGROUND

The present disclosure relates to a wearable device for measuring an edema index and a method of measuring an edema index using the same.

This application comes from research [Project Management No. 1711035203(R0992-16-1021), Project Name: Development of Energy Harvesting and Wireless Power Transmission Technology for a Wearable Device], conducted as part of training business of human resources for information communications technology in the Ministry of Science, ICT and Future Planning and the Institute for Information & Communications Technology Promotion.

Recently, with advances in medicine and the extension of average human lifespans, interest in health management is growing. Accordingly, demand for medical devices for health administration is also rising.

Body composition measuring instruments, a type of healthcare device, commonly measure body compositions using bioelectrical impedance analysis (BIA). Using BIA, the impedance of the human body may be measured by considering the human organism as a combination of impedances, applying current to the human body, and measuring voltage generated by the applied current, and body compositions such as water, proteins, calcium, and fat comprising bodies may be analyzed from the measured impedance.

However, such healthcare devices may only measure simple biometric data such as body compositions, and may not be able to measure specific indices, such as an edema index and the like. The amount of total body water falls into intracelluar fluid and extracellular fluid, and the ratio of the extracellular fluid to total body water is referred to as an "edema index." Edema is a state of imbalance of water in and out of cells, and when undernourishment due to aging, low muscular obesity, water imbalance caused by diseases, and temporary fatigue and swelling occur, an edema index may be increased.

Furthermore, healthcare devices such as those mentioned above may not be able to measure an edema index due to having too much volume and weight to function as a portable device.

SUMMARY

An aspect of the present disclosure may provide a wearable device for measuring an edema index, which is easy to carry and may easily measure the edema index, and a method of measuring an edema index using the same.

According to an aspect of the present disclosure, a wearable device for measuring an edema index may include: a band, wearable on a wrist; an electrode module including a pair of current electrodes and a pair of voltage electrodes; and a main module applying an alternating current (AC) to the pair of current electrodes, and obtaining an edema index of a human body from an AC voltage measured from the pair of voltage electrodes, wherein each of the pair of current electrodes and the pair of voltage electrodes may be attached to one surface of the band in a row in a length direction of the band, and may protrude from the surface of the band to be in direct contact with the skin of the wrist when the band is worn on the wrist.

According to an aspect of the present disclosure, a method of measuring an edema index using a wearable device, the wearable device including a band, wearable on a wrist, and an electrode module having a pair of current electrodes and a pair of voltage electrodes respectively attached to one surface of the band in a row in a length direction of the band, and respectively protruding from the surface of the band to be in direct contact with the skin of the wrist when the band is worn on the wrist, the method may include: receiving user information including the weight, gender, and height of a user; applying an AC to the pair of current electrodes; measuring an AC voltage through the pair of voltage electrodes; and obtaining an edema index, based on the user information, the applied AC, and the measured AC voltage, in which the edema index is obtained using the following formula:

$$EI = \frac{ECW}{TBW}$$

$$ECW = -5.22 + \frac{0.2 \times ht^2}{R_f} + \frac{0.005 \times ht^2}{X_{cf}} + 0.08 \times \text{wt} + 1.9 + 1.86 \times \text{sex}$$

$$TBW = 0.73 \times \left(-4.104 + \frac{0.518 \times ht^2}{R_f} + 0.23 \times \text{wt} + 0.13 \times X_{cf} + 4.229 \times \text{sex},\right.$$

in which EI is defined as an edema index, ECW is defined as an in vitro cell water content, TBW is defined as a total human body water content, ht is defined as the height of a user, $R_f$ is defined as the resistance of biometric impedance obtained from the applied AC and the measured AC voltage in a fKHz frequency, $X_{cf}$ is defined as the capacitive reactance of the biometric impedance obtained from the applied AC and the measured AC voltage in the fKHz frequency, wt is defined as the weight of the user, and sex is defined as the gender of the user with values 1 and 2 denoting male and female, respectively.

BRIEF DESCRIPTION OF DRAWINGS

The above and other aspects, features, and advantages of the present disclosure will be more clearly understood from the following detailed description taken in conjunction with the accompanying drawings, in which.

DETAILED DESCRIPTION

Figure 1A:
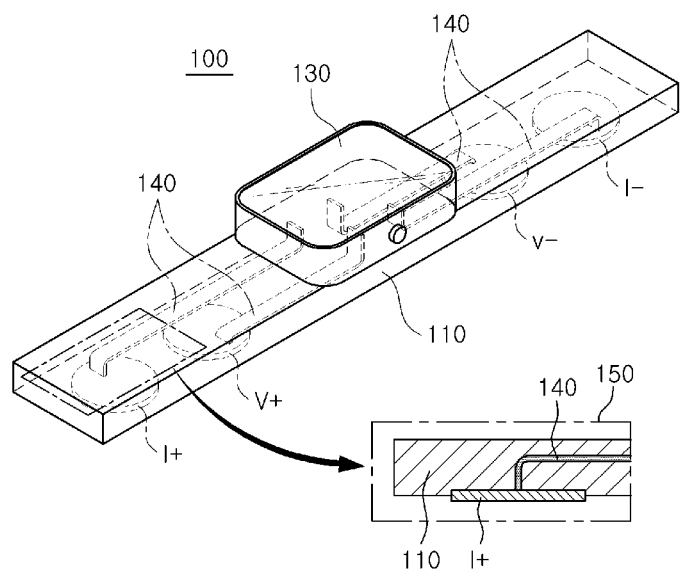
FIG. 1A is a front perspective view of a wearable device for measuring an edema index according to an embodiment.

Hereinafter, embodiments of the present disclosure will be described as follows with reference to the attached drawings.

The present disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

Throughout the specification, it will be understood that when an element, such as a layer, region or wafer (substrate), is referred to as being "on," "connected to," or "coupled to" another element, it can be directly "on," "connected to," or "coupled to" the other element or other elements intervening therebetween may be present. In contrast, when an element is referred to as being "directly on," "directly connected to," or "directly coupled to" another element, there may be no other elements or layers intervening therebetween. Like numerals refer to like elements throughout. As used herein, the term "and/or" includes any and all combinations of one or more of the associated listed items.

It will be apparent that though the terms first, second, third, etc. may be used herein to describe various members, components, regions, layers and/or sections, these members, components, regions, layers and/or sections should not be limited by these terms. These terms are only used to distinguish one member, component, region, layer or section from another region, layer or section. Thus, a first member, component, region, layer or section discussed below could be termed a second member, component, region, layer or section without departing from the teachings of the exemplary embodiments.

Spatially relative terms, such as "above," "upper," "below," and "lower" and the like, may be used herein for ease of description to describe one element's relationship relative to another element(s) as shown in the figures. It will be understood that the spatially relative terms are intended to encompass different orientations of the device in use or operation in addition to the orientation depicted in the figures. For example, if the device in the figures is turned over, elements described as "above," or "upper" relative to other elements would then be oriented "below," or "lower" relative to the other elements or features. Thus, the term "above" can encompass both the above and below orientations depending on a particular direction of the figures. The device may be otherwise oriented (rotated 90 degrees or at other orientations) and the spatially relative descriptors used herein may be interpreted accordingly.

The terminology used herein describes particular embodiments only, and the present disclosure is not limited thereby. As used herein, the singular forms "a," "an," and "the" are intended to include the plural forms as well, unless the context clearly indicates otherwise. It will be further understood that the terms "comprises," and/or "comprising" when used in this specification, specify the presence of stated features, integers, steps, operations, members, elements, and/or groups thereof, but do not preclude the presence or addition of one or more other features, integers, steps, operations, members, elements, and/or groups thereof.

Hereinafter, embodiments of the present disclosure will be described with reference to schematic views illustrating embodiments of the present disclosure. In the drawings, for example, due to manufacturing techniques and/or tolerances, modifications of the shape shown may be estimated. Thus, embodiments of the present disclosure should not be construed as being limited to the particular shapes of regions shown herein, for example, to include a change in shape results in manufacturing. The following embodiments may also be constituted by one or a combination thereof.

The contents of the present disclosure described below may have a variety of configurations and propose only a required configuration herein, but are not limited thereto.

Figure 1B:
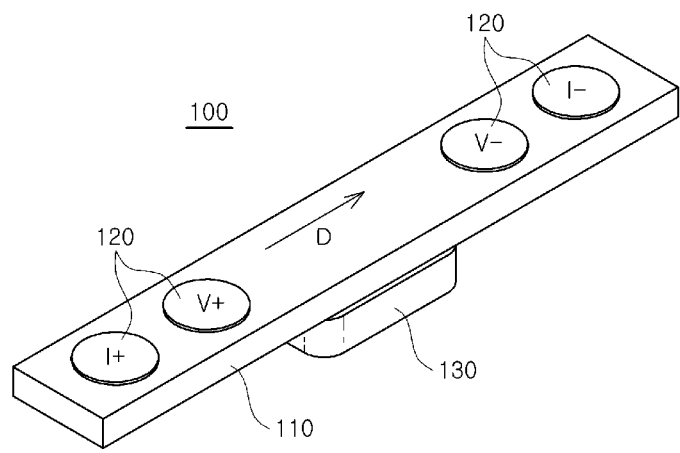
FIG. 1B is a rear perspective view of the wearable device of FIG. 1A.
Figure 2:
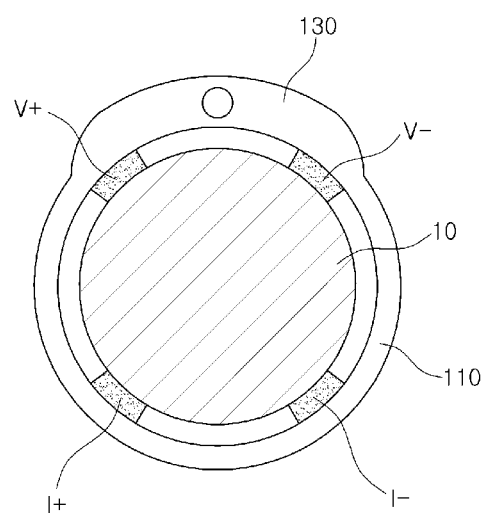
FIG. 2 is a view of a wearable device according to an embodiment, worn on a wrist.
Figure 3A:
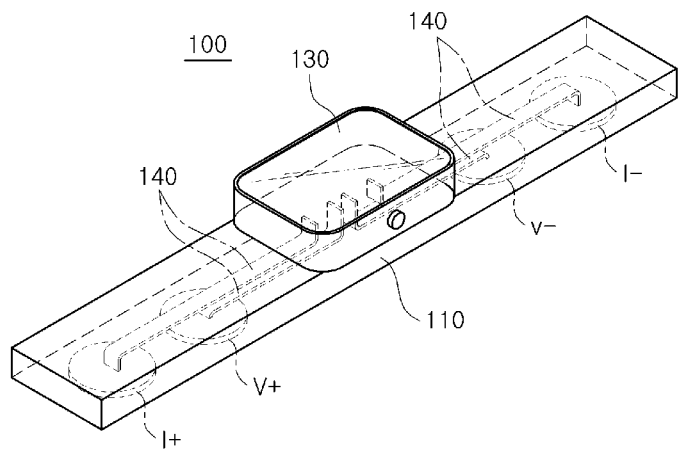
FIG. 3A is a front perspective view of a conductive wire according to an embodiment.
Figure 3B:
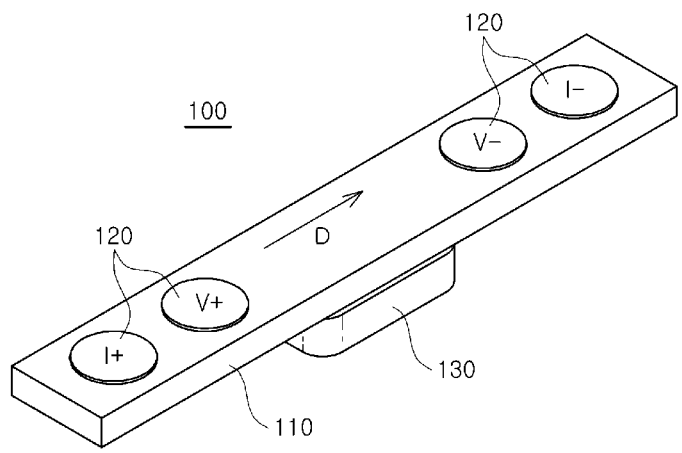
FIG. 3B is a rear perspective view of the conductive wire of FIG. 3A.
Figure 4:
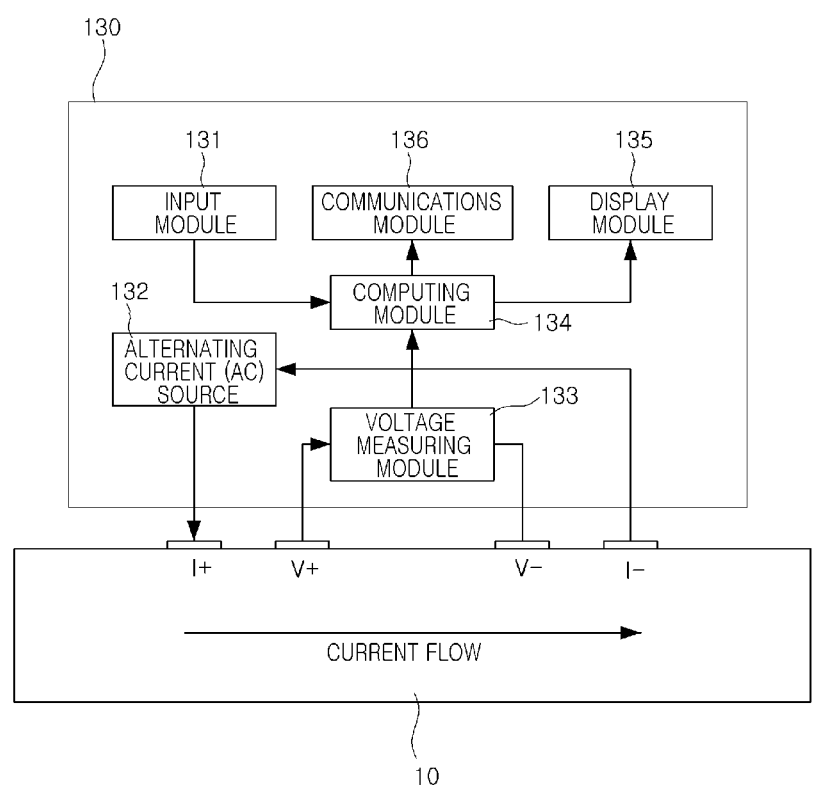
FIG. 4 is a diagram illustrating the operating principle of a main module according to an embodiment.

FIGS. 1A and 1B are diagrams of a wearable device for measuring an edema index according to an embodiment. FIG. 1A is a diagram of the wearable device viewed from above. FIG. 1B is a diagram of the wearable device viewed from below. FIG. 2 is a view of a wearable device according to an embodiment, worn on a wrist. FIG. 3A is a front perspective view of a conductive wire according to an embodiment. FIG. 3B is a rear perspective view of the conductive wire of FIG. 3A. FIG. 4 is a diagram illustrating the operating principle of a main module according to an embodiment.

As illustrated in FIGS. 1A, 1B, and 2, a wearable device 100 of measuring an edema index according to an embodiment may include a band 110 wearable on a wrist, an electrode module 120 being in direct contact with the skin of the wrist when the band 110 is worn on the wrist, and a main module 130 applying an alternating current (AC) to a human body through the electrode module 120, and obtaining an edema index based on an AC voltage measured through the electrode module 120.

In detail, the band 110 may be formed of a flexible material such as rubber that may be pliable so as to be wearable on a wrist 10 of a human body, and may have a thickness and length.

The band 110 may have the electrode module 120 attached to one surface thereof. The electrode module 120 may include a pair of current electrodes I+ and I− applying an AC and a pair of voltage electrodes V+ and V− measuring an AC voltage.

In detail, as illustrated in FIG. 1B, the electrode module 120 may be attached to a surface of the band 110 in a length direction D of the band 110, and may protrude from the band 110, thus being in direct contact with the skin of the wrist 10 when the band 110 is worn thereon. In particular, the pair of voltage electrodes V+ and V− may be disposed between the pair of current electrodes I+ and I−. Further, the electrode module 120 may be a silver-coated electrode so as not to irritate the skin of the wrist 10. The shape of the electrode module 120 may also be circular, but this is merely to help in understanding the present disclosure, and it should be noted that the electrode module 120 may be implemented in various shapes, such as an oval shape.

The band 110 may further include conductive wires 140 therein to connect the pair of current electrodes I+ and I− to the main module 130 and connect the pair of voltage electrodes V+ and V− to the main module 130.

According to an embodiment, the conductive wires 140 may be disposed parallel to each other on the same plane inside the band 110, as illustrated in FIG. 1A.

Further, according to an embodiment, the conductive wires 140 may be disposed on different planes inside the band 110, as illustrated in FIG. 3A. For example, conductive wires connecting the pair of current electrodes I+ and I− to the main module 130 may be disposed on the same plane, and conductive wires connecting the pair of voltage electrodes V+ and V− to the main module 130 may be disposed on a plane disposed below the same plane.

A disposition of the conductive wires 140 is for the purpose of understanding of the present disclosure, and it should be noted that the conductive wires 140 are not limited to the disposition.

The main module 130 may control an AC source 132 to apply an AC to the pair of current electrodes I+ and I−, and may obtain an edema index of the human body from an AC voltage measured through a voltage measuring module 133 and the pair of voltage electrodes V+ and V− according to the following Formula 1.

$$EI = \frac{ECW}{TBW} \quad \text{[Formula 1]}$$

$$ECW = -5.22 + \frac{0.2 \times ht^2}{R_f} + \frac{0.005 \times ht^2}{X_{cf}} + 0.08 \times wt + 1.9 + 1.86 \times sex$$

$$TBW = 0.73 \times \left( -4.104 + \frac{0.518 \times ht^2}{R_f} + 0.23 \times wt + 0.13 \times X_{cf} + 4.229 \times sex \right)$$

Here, EI is defined as an edema index, ECW is defined as an in vitro cell water content, TBW is defined as a total human body water content, ht is defined as the height of a user, $R_f$ is defined as the resistance of biometric impedance obtained from an AC and an AC voltage in a fKHz frequency, $X_{cf}$ is defined as the capacitive reactance of the biometric impedance obtained from the AC and the AC voltage in the fKHz frequency, wt is defined as the weight of the user, and sex is defined as the gender of the user with values 1 and 2 denoting male and female, respectively.

For this purpose, the main module 130, as illustrated in FIG. 4, may be attached to the other surface of the band 110, and may include the AC source 132 applying an AC to the current electrodes I+ and I−, the voltage measuring module 133 measuring the phase and level of an AC voltage measured through the voltage electrodes V+ and V−, a computing module 134 obtaining an edema index from the applied AC and the measured phase and level of the AC voltage, based on the Formula 1, a display module 135 displaying the obtained edema index, an input module 131 receiving user information, and a communications module 136 transmitting the obtained edema index to an external source through wireless communications.

Here, the user information may include at least the height, gender, and weight of a user. Further, a frequency of an AC applied by the AC source 132 may have a value of 60 μA to 100 μA.

As described above, according to an embodiment, a device for measuring an edema index may be provided in the form of a band, wearable on a wrist, thus being easy to carry and easily measuring the edema index.

Figure 5:
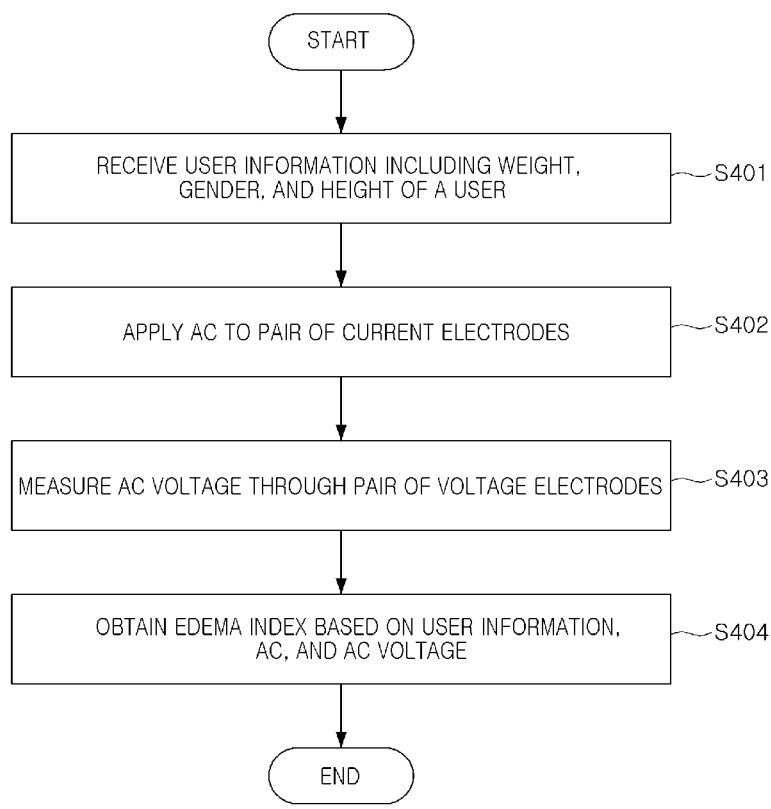
FIG. 5 is a flow chart of a method of measuring an edema index according to an embodiment.

FIG. 5 is a flow chart of a method of measuring an edema index according to an embodiment. For simplicity of the present disclosure, descriptions overlapping with those of FIGS. 1 through 4 will be omitted.

As illustrated in FIGS. 4 and 5, a method of measuring an edema index according to an embodiment may start from receiving user information including the weight, gender, and height of a user (S501). The user information, as described above, may at least include the height, gender, and weight of the user, which may be input through the input module 131 of the main module 130.

Subsequently, the AC source 132 may apply an AC to the pair of current electrodes I+ and I− (S502). The AC may flow from the current electrode 1+ to the current electrode I− with a current flow.

Next, the voltage measuring module 133 may measure an AC voltage, for example, the phase and level of the AC voltage, through the voltage electrodes V+ and V− (S503).

Finally, the main module 130 may obtain an edema index, based on the user information, the applied AC, and the measured phase and level of the AC voltage (S504). The obtaining of the edema index according to the Formula 1 may be the same as described above.

As set forth above, according to an exemplary embodiment, a device of measuring an edema index may be provided in the form of a band, wearable on the wrist, thus being easy to carry and easily measuring the edema index.

While exemplary embodiments have been shown and described above, it will be apparent to those skilled in the art that modifications and variations could be made without departing from the scope of the present invention as defined by the appended claims.

What is claimed is:

1. A wearable device for measuring an edema index comprising:
  a band, wearable on a wrist;
  an electrode module including a pair of current electrodes and a pair of voltage electrodes; and
  a main module including an alternating current (AC) source connected to the pair of current electrodes for applying an alternating current (AC) to the pair of current electrodes, and a computing module configured to obtain an edema index of a human body from an AC voltage measured through the pair of voltage electrodes,
  wherein each of the pair of current electrodes and the pair of voltage electrodes is attached to a first surface of the band in a row in a length direction of the band, and protrudes from the first surface of the band to be in direct contact with the skin of the wrist when the band is worn on the wrist, and
  wherein the edema index is calculated by the computing module using the following formula:

$$EI = \frac{ECW}{TBW}$$

$$ECW = -5.22 + \frac{0.2 \times ht^2}{R_f} + \frac{0.005 \times ht^2}{X_{cf}} + 0.08 \times wt + 1.9 + 1.86 \times sex$$

$$TBW = 0.73 \times \left( -4.104 + \frac{0.518 \times ht^2}{R_f} + 0.23 \times wt + 0.13 \times X_{cf} + 4.229 \times sex \right),$$

wherein EI is defined as an edema index, ECW is defined as an vitro cell water content, TBW is defined as a total human body water content, ht is defined as the height of a user, $R_f$ is defined as the resistance of biometric impedance obtained from the applied AC and the measured AC voltage in fKHz frequency $X_{cf}$ is defined as the capacitive reactance of the biometric impedance obtained from the applied AC and the measured AC voltage in the fKHz frequency, wt is defined as the weight of the user, and sex is defined as the gender of the user with values 1 and 2 denoting male and female respectivey.

2. The wearable device of claim 1, wherein the main module is attached to another surface of the band opposite the first surface, and comprises a voltage measuring module connected to the pair of voltage electrodes for measuring the phase and level of an AC voltage through the pair of voltage electrodes, a display module connected to the computing module and configured to display the edema index, and an input module configured to receive user information.

3. The wearable device of claim 1, wherein the pair of voltage electrodes are disposed between the pair of current electrodes.

4. The wearable device of claim 1, further comprising conductive wires connecting the pair of current electrodes to the main module, and connecting the pair of voltage electrodes to the main module,
wherein the conductive wires are disposed on a common plane or on different planes inside the band.

5. The wearable device of claim 1, wherein the frequency of the AC is between 10 Khz and 200 KHz, and the level of the AC is between 60 μA and 100 μA.

6. A method of measuring an edema index using a wearable device, the wearable device comprising a band, wearable on a wrist, and an electrode module having a pair of current electrodes and a pair of voltage electrodes respectively attached to a first surface of the band in a row in a length direction of the band, and respectively protruding from the first surface of the band to be in direct contact with the skin of the wrist when the band is worn on the wrist, the method comprising:
receiving user information including the weight, gender, and height of a user;
applying an alternating current (AC) to the pair of current electrodes;
measuring an AC voltage through the pair of voltage electrodes; and
obtaining an edema index, based on the user information, the applied AC, and the measured AC voltage,
wherein the edema index is obtained using the following formula:

$$EI = \frac{ECW}{TBW}$$

$$ECW = -5.22 + \frac{0.2 \times ht^2}{R_f} + \frac{0.005 \times ht^2}{X_{cf}} + 0.08 \times wt + 1.9 + 1.86 \times sex$$

$$TBW = 0.73 \times \left(-4.104 + \frac{0.518 \times ht^2}{R_f} + 0.23 \times wt + 0.13 \times X_{cf} + 4.229 \times sex\right),$$

wherein EI is defined as an edema index, ECW is defined as an in vitro cell water content, TBW is defined as a total human body water content, ht is defined as the height of a user, $R_f$ is defined as the resistance of biometric impedance obtained from the applied AC and the measured AC voltage in a fKHz frequency, $X_{cf}$ is defined as the capacitive reactance of the biometric impedance obtained from the applied AC and the measured AC voltage in the fKHz frequency, wt is defined as the weight of the user, and sex is defined as the gender of the user with values 1 and 2 denoting male and female, respectively.

\* \* \* \* \*